United States Patent [19]

Grollier et al.

[11] Patent Number: 5,192,534
[45] Date of Patent: Mar. 9, 1993

[54] COMPOSITION FOR INDUCING AND STIMULATING HAIR GROWTH AND/OR RETARDING ITS LOSS, BASED ON PYRIMIDINE DERIVATIVES AND SUNSCREENS

[75] Inventors: Jean F. Grollier; Isabelle Richoux, both of Paris, France

[73] Assignee: L'Oreal, Paris, France

[21] Appl. No.: 834,977

[22] Filed: Feb. 13, 1992

Related U.S. Application Data

[63] Continuation of Ser. No. 459,128, Dec. 29, 1989, abandoned.

[30] Foreign Application Priority Data

Dec. 30, 1988 [FR] France ................... 88 17466

[51] Int. Cl.$^5$ .............................................. A61K 7/42
[52] U.S. Cl. ................................. 424/59; 424/60; 514/256
[58] Field of Search ............... 424/60, 59; 514/256

[56] References Cited

U.S. PATENT DOCUMENTS

| | | | |
|---|---|---|---|
| 4,013,778 | 3/1977 | Morrison | 514/256 |
| 4,454,112 | 6/1984 | Tuominen | 424/60 |
| 4,489,057 | 12/1984 | Welters | 424/60 |
| 4,820,512 | 4/1989 | Grollier | 514/256 |

FOREIGN PATENT DOCUMENTS

WO8302558  8/1983  World Int. Prop. O.

Primary Examiner—Thurman K. Page
Assistant Examiner—William E. Benston, Jr.
Attorney, Agent, or Firm—Jacobson, Price, Holman & Stern

[57] ABSTRACT

The invention relates to a composition intended for inducing and stimulating hair growth and decreasing its loss, containing, in a physiologically acceptable medium, at least one pyrimidine derivative corresponding to the formula:

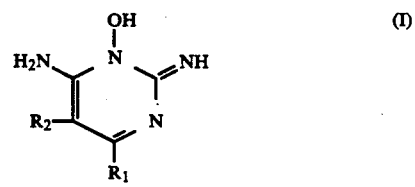

(I)

in which $R_1$ denotes

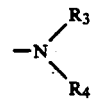

where $R_3$ and $R_4$ are hydrogen, lower cycloalkyl, alkyl, alkenyl or alkylaryl, it also being possible for $R_3$ and $R_4$, with the nitrogen atom to which they are attached, to form a heterocycle, preferably piperidyl, and $R_2$ is preferably hydrogen, as well as its addition salts with physiologically acceptable acids; and at least one agent screening out UV radiation, selected from 2-hydroxy-4-methoxybenzophenone, 2-ethylhexyl para-dimethylaminobenzoate, pentyl para-dimethylaminobenzoate, 2-ethylhexylpara-methoxycinnamate, 4-(1,1-dimethylethyl)-4'-methoxydibenzoylmethane, N-(2-ethylhexyl)-3-[(3'-methoxy-4'-n-butoxy)benzylidene]-10-camphorsulphonamide, 3-(4-methylbenzylidene)camphor, homomenthyl salicylate, 2-ethylhexyl salicylate, para-aminobenzoic acid and 2-hydroxy-4-methoxybenzophenone-5-sulphonic acid, as well as mixtures thereof.

31 Claims, No Drawings

COMPOSITION FOR INDUCING AND STIMULATING HAIR GROWTH AND/OR RETARDING ITS LOSS, BASED ON PYRIMIDINE DERIVATIVES AND SUNSCREENS

This application is a continuation of application Ser. No. 459,128, filed Dec. 29, 1989, now abandoned.

The invention relates to new compositions for inducing and stimulating hair growth and/or retarding its loss, containing, in combination, pyrimidine derivatives and at least some agents screening out UV radiation.

Compositions enabling alopecia to be abolished and reduced and, in particular, hair growth to be induced and stimulated and/or its loss to be decreased have been sought for many years in the cosmetics or pharmaceutical industry.

Alopecia, as is well known, is due, in particular, to a disturbance of the hair cycle, inasmuch as it is generally found to occur when the growth phase known as the "anagen phase" is shortened, as a result of which transition of hairs to the telogen phase occurs earlier and the hairs fall in larger numbers.

Successive growth cycles result in increasingly finer and increasingly shorter hairs, gradually converting to an unpigmented down which can lead to baldness.

The changes in these different categories of hair may be determined by means of a trichogram, and especially a phototrichogram.

In this connection, compounds such as 6-amino-1,2-dihydro-1-hydroxy-2-imino-4-piperidinopyrimidine and its derivatives have already been proposed. Such compounds are described, more especially, in U.S. Pat. No. 4,139,619.

In Application WO-A-83/02,558, compositions based on retinoids and minoxodil, used, in particular, for stimulating human hair growth and treating some types of alopecia, have also been described.

It was, however, found that 6-amino-1,2-dihydro-1-hydroxy-2-imino-4-piperidinopyrimidine, also known by the name of minoxidil, displayed problems of solubilization, as a result of which lotions recommended for topical application to the scalp generally contained this compound in the solubilized state only at relatively low concentrations.

Means have hence been sought which are capable of advantageously modifying the solubility of these pyrimidine derivatives, both to permit more rapid dissolution of the active substance and to prevent recrystallization of the latter in the course of time, in particular crystallization of minoxidil on the scalp brought about by evaporation of the solvent, thereby leading to a loss of active substance through a phenomenon of powdering, the cosmetic effect of which is, in addition, undesirable, or to permit the use of concentrated solutions of minoxidil which can be diluted at the time of use with other compositions containing active substances.

Moreover, and inasmuch as these compositions are intended for topical application to the scalp and this application is generally not followed by a rinsing step, it has proved essential to perform the solubilization of the active substance with cosolubilizing agents whose effects on the hair of the treated individuals are cosmetic, that is to say they do not lead to the hair becoming gummy, sticky or greasy.

Agents screening out UV radiation, generally used for the protection of the human epidermis, in particular for preserving the skin from the adverse effects of ultraviolet radiation, have, moreover, been known for a long time.

The Applicant discovered, and this forms the subject of the invention, that, surprisingly, some agents screening out UV radiation, protecting the scalp of alopecic subjects which is directly exposed to the possibly adverse effects of UV radiation, also enabled, in the case of some of these agents, improved solubilization of the pyrimidine derivatives to be obtained.

This effect is especially surprising when it is realized that the sunscreen properties are completely unrelated to the cosolubilization properties of these sunscreen agents.

A subject of the invention hence consists of a combination of pyrimidine derivatives and certain agents screening out UV radiation, in a composition intended for inducing and stimulating hair growth and decreasing its loss.

Another subject of the invention consists of cosmetic and/or pharmaceutical compositions containing such a combination.

A subject of the invention also consists of treatment processes employing such a combination, as well as devices for the use of the combination.

Other subjects of the invention will become apparent on reading the description and the examples which follow.

The composition intended for inducing or stimulating hair growth and decreasing its loss, according to the invention, is essentially characterized in that it contains, in a physiologically acceptable medium, at least one pyrimidine derivative corresponding to the formula:

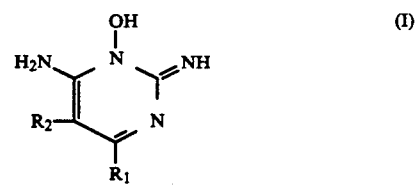

in which $R_1$ denotes a group

in which $R_3$ and $R_4$ may be selected from hydrogen and a lower cycloalkyl, alkyl, alkenyl or alkylaryl group, it also being possible for $R_3$ and $R_4$, with the nitrogen atom to which they are attached, to form a heterocycle selected, inter alia, from aziridinyl, azetidinyl, pyrrolidinyl, piperidyl, hexahydroazepinyl, heptamethylenimine, octamethylenimine, morpholine and 4-(lower alkyl)piperazinyl groups, it being possible for the heterocyclic groups to be substituted on the carbon atoms with one to three lower alkyl, hydroxy or alkoxy groups; and the group $R_2$ is selected from hydrogen and a lower haloarylalkyl, alkyl, alkenyl, alkylalkoxy, cycloalkyl, aryl, alkylaryl, arylalkyl, alkylarylalkyl or alkoxyarylalkyl group; as well as the addition salts with physiologically acceptable acids;

and at least one agent screening out UV radiation, selected from the following compounds:

2-hydroxy-4-methoxybenzophenone;

2-ethylhexyl para-dimethylaminobenzoate;
pentyl para-dimethylaminobenzoate;
2-ethylhexyl para-methoxycinnamate;
4-(1,1-dimethylethyl)-4'-methoxydibenzoylmethane;
N-(2-ethylhexyl)-3-[(3'-methoxy-4'-n-butoxy)benzylidene]-10-camphorsulphonamide;
3-(4-methylbenzylidene)camphor;
homomenthyl salicylate;
2-ethylhexyl salicylate;
para-aminobenzoic acid; and
2-hydroxy-4-methoxybenzophenone-5-sulphonic acid;
as well as mixtures thereof.

In the formula (I), the alkyl or alkoxy groups preferably denote a group having 1 to 4 carbon atoms; alkenyl preferably denotes a group having 2 to 5 carbon atoms; aryl preferably denotes phenyl; the cycloalkyl group preferably denotes a group having between 4 and 6 carbon atoms; halogen preferably denotes chlorine or bromine.

More especially preferred compounds of formula (I) are selected from the compounds in which $R_2$ denotes hydrogen and $R_1$ denotes a group:

in which $R_3$ and $R_4$ form a piperidyl ring, as well as their salts such as, for example, the sulphate. The especially preferred compound consists of 6-amino-1,2-hydro-1-hydroxy-2-imino-4-piperidinopyrimidine, also known as "minoxidil".

The pyrimidine derivatives of formula (I) are used according to the invention in proportions preferably of between 0.1 and 10% by weight, and more especially between 1 and 5% by weight, relative to the total weight of the composition.

The agents screening out UV radiation, defined above, are preferably present in proportions sufficient to increase the solubility of the pyrimidine derivative of formula (I) in the medium in question, this increase preferably being greater than 10%, and especially greater than 20%, relative to the solubility of the pyrimidine derivative of formula (I) in this medium.

The agents screening out UV solar radiation are preferably used in proportions of between 0.1 and 10%, and preferably between 0.3 and 4%, relative to the total weight of the composition.

The compositions according to the invention may be aqueous or alternatively anhydrous, the aqueous or anhydrous medium being physiologically acceptable.

Aqueous medium denotes a medium consisting of water or a mixture of water and a physiologically acceptable solvent.

Anhydrous medium, according to the invention, denotes a solvent medium containing less than 1% of water. This anhydrous medium can consist of a solvent or mixture of solvents selected, more especially, from $C_2$-$C_4$ lower alcohols such as ethyl alcohol, alkylene glycols such as propylene glycol, and alkylene glycol or dialkylene glycol alkyl ethers, the alkyl or alkylene radicals being radicals having 1 to 4 carbon atoms.

These same solvents, in particular ethyl alcohol, may be used in the aqueous medium.

The compositions according to the invention can also contain different adjuvants customarily used in compositions intended for topical application in cosmetics or pharmacy, including preservatives, colourings and fragrances.

These compositions can also contain thickening agents well known in the prior art.

An especially advantageous embodiment of the invention consists in using, in addition to the pyrimidine derivative and the sunscreen agent, at least one retinoid which can either be used in combination in the same composition or in a mixture with the composition defined above at the time of use, or be used in a sequential application before or after application of the composition containing the pyrimidine derivative and the sunscreen agent, successively or separated by an interval of time.

The retinoids are, in particular, selected from the compounds corresponding to the formula:

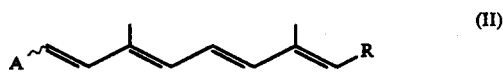

in which:
a) A is a group selected from the groups of formulae:

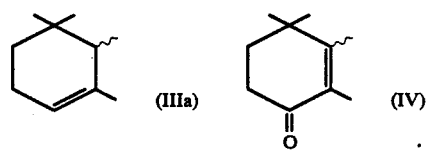

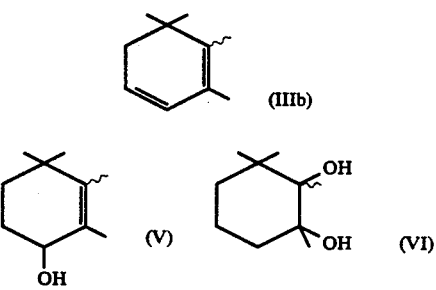

in which:
when A denotes a group of formula (IIIa), R is selected from the following groups:
CHO; CH$_2$OR$_5$,
in which R$_5$ denotes hydrogen or. C$_1$-C$_4$ lower alkyl;
a group

where R$_6$ denotes C$_1$-C$_{16}$ linear or branched alkyl; CH$_2$SR$_7$, in which R$_7$ denotes hydrogen or methyl;

in which X denotes:
(i) OH;
(ii) OR$_6$, where R$_8$ denotes a C$_1$-C$_{15}$ alkyl radical, C$_1$-C$_4$ arylalkyl radical optionally substituted on the aryl group, C$_1$-C$_4$ arylcarboxyalkyl radical optionally substituted on the aryl group, or $C_1$-$C_4$ hydroxyalkyl or $C_1$-$C_4$ amidoalkyl radical;

(iii) $NR_9R_{10}$, in which $R_9$ and $R_{10}$, which may be identical or different, denote hydrogen, $C_1$-$C_6$ alkyl, $C_1$-$C_4$ hydroxyalkyl or optionally substituted aryl;

it being possible for $R_9$ or $R_{10}$ to represent an optionally substituted heterocycle or, together with the nitrogen atom to which they are attached, to form a heterocycle which is itself optionally substituted;

(iv) an $N_3$ group;

or alternatively a group of formula $CH_2NHR_{11}$, in which $R_{11}$ denotes an optionally substituted benzoyl radical;

when A denotes a group of formula (IIIb), (IV), (V) or (VI), $R_1$ denotes COOH as well as its salified or esterified form;

b) A is a group selected from aryl or substituted aryl groups, a heterocycle or substituted heterocycle, an aryl-heterocyclic group optionally substituted on the heterocycle or an aryl-homocyclic group optionally substituted on the aromatic ring, R in this case denoting a COOH group, a group $COOR_{12}$ where $R_{12}$ denotes a $C_1$-$C_4$ alkyl radical or alternatively an amide group substituted with a $C_1$-$C_4$ alkyl group, as well as their physiologically acceptable salts and esters.

In the abovementioned formula, $C_1$-$C_4$ alkyl preferably denotes methyl, ethyl, n-butyl or t-butyl; $C_1$-$C_{16}$ alkyl preferably denotes ethyl, propyl or palmityl; aryl preferably denotes phenyl or benzyl, and the substituents on the aryl groups are preferably $C_1$-$C_4$ alkyl, $C_1$-$C_{12}$ alkoxy, hydroxyl, halogen or nitro groups, it being possible for the alkoxy or alkyl groups themselves to be optionally substituted with an OH group.

The heterocyclic groups may be selected, inter alia, from groups derived from phthalimide, from succinimide and from 4- to 6-membered heterocycles containing one or more oxygen atoms, one or more nitrogen atoms.

The compounds of the retinoid family, defined above, are, in particular, selected from: retinal, retinol, retinyl acetate, propionate and palmitate, retinoic acid in all-trans, 13-cis, 9-cis, 11-cis, 9,13-dicis and 11,13-dicis forms, the corresponding zinc retinoates and the quaternary ammonium retinoates of formula:

in which $X^\ominus$ denotes an all-trans- or 13-cis-retinoate radical; and (i) $R_{13}$, $R_{14}$ and $R_{15}$, which may be identical or different, denote a $C_1$-$C_4$ linear alkyl group which can bear one or more hydroxyl group(s) in the chain, $R_{16}$ denoting $C_{12}$-$C_{18}$ linear alkenyl or alkyl;

(ii) $R_{15}$ denotes a group:

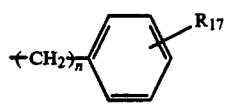

in which:

n is equal to 0 or 1, $R_{17}$ represents a hydrogen or halogen atom or a hydroxyl, $C_1$-$C_{18}$ alkyl or hydroxyalkyl or $C_2$-$C_{18}$ acyl group;

$R_{13}$, $R_{14}$ and $R_{15}$ having the meanings stated under (i);

(iii) $R_{13}$ and $R_{14}$ can form an aliphatic heterocycle containing at least one oxygen atom, one nitrogen atom or one sulphur atom;

$R_{15}$ or $R_{16}$ having the meanings stated under (i) and (ii).

Other compounds falling within the definition of retinoids which are especially usable according to the invention are selected from: all-trans-retinoyloxyacetamide, a mixture of 2-hydroxy-1-propyl and 1-hydroxy-2-propyl all-trans-retinoates, 2-hydroxyethyl all-trans-retinoate, 4-nitrobenzyl all-trans-retinoate, benzyl all-trans-retinoate, 4-(all-trans-retinoyloxyacetyl)catechol, 2-cyclohexylethyl all-trans-retinoate, 10-carboxymethyldecyl all-trans-retinoate, 4-hydroxybutyl all-trans-retinoate, cholesteryl all-trans-retinoate, 4-bromobenzyl all-trans-retinoate, cholesteryl all-trans-retinoyloxyacetate, all-trans-retinoyloxyacetylbenzene, 4-(all-trans-retinoyloxyacetyl)bromobenzene, 4-(all-trans-retinoyloxyacetyl)nitrobenzene, 4-(all-trans-retinoyloxyacetyl)benzonitrile, all-trans-retinoyloxyacetyl-2,4-dichlorobenzene, N-(all-trans-retinoyloxy)phthalimide, N-(all-trans-retinoyloxy)succinimide, 4-(all-trans-retinoyloxyacetyl)methoxybenzene, 4-(all-trans-retinoyloxyacetyl)phenol, 4-(all-trans-retinoyloxyacetyl)-3,4,5-trimethoxybenzene, 4-(all-trans-retinoyloxyacetyl)-2,4,6-trimethylbenzene, 4-(all-trans-retinoyloxyacetyl)toluene, 4-(all-trans-retinoyloxyacetyl)ethoxybenzene, 4-(all-trans-retinoyloxyacetyl)acetoxybenzene, 4-(all-trans-retinoyloxyacetyl)naphthalene, 4-(all-trans-retinoyloxyacetyl)biphenyl, 4-(all-trans-retinoyloxyacetyl)-2,5-dimethoxybenzene, 1-(all-trans-retinoyloxyacetyl)-2,4-dimethylbenzene, 1-(all-trans-retinoyloxyacetyl)-3,4-diacetoxybenzene, all-trans-retinamide, 2-hydroxyethyl all-trans-retinamide, N-ethyl-all-trans-retinamide, 4-(all-trans-retinoyl)aminophenol, N-(methyldimethyldioxolane)-retinamide, N-(ortho-carboxyphenyl)retinamide, N-(p-carboxyphenyl)retinamide, N-hydroxypropyl-all-trans-retinamide, N-(hydroxypropyl)-13-cis-retinamide, N-(5-tetrazolyl)-all-trans-retinamide, N-(5-tetrazolyl)-13-cis-retinamide, N-(3,4 methylenedioxyphenylmethyl)-all-trans-retinamide, N-(n-propyl)-all-trans-retinamide, N-tert-butyl-all-trans-retinamide, N-(1,1,3,3-tetramethylbutyl)-all-trans-retinamide, N-(4-carboxymethyl-3-hydroxyphenyl)-all-trans-retinamide, N-[β-(3,4-dimethoxyphenyl)ethyl]-all-trans-retinamide, 2-(all-trans-retinoylamino)benzotriazole, 1-(all-trans-retinoyl)-1,2,4-triazole, N-(all-trans-retinoyl)imidazole, 1-nicotinoyl-2-(all-trans-retinoyl)hydrazine, N-(all-trans-retinoyl)morpholine, trans-β-ionone (all-trans-retinoyl)hydrazone, N,N'-dicyclohexyl-N-(all-trans-retinoyl)urea, acetone (all-trans-retinoyl)hydrazone, N-benzoylretinylamine and retinoyl azide.

The groups represented by A and defined above in paragraph (b) in connection with the aryl, substituted aryl, heterocyclic or substituted heterocyclic groups, aryl-heterocyclic groups substituted on the heterocyclic or aryl-homocyclic groups substituted on the aromatic ring are, in particular, selected from the following groups:

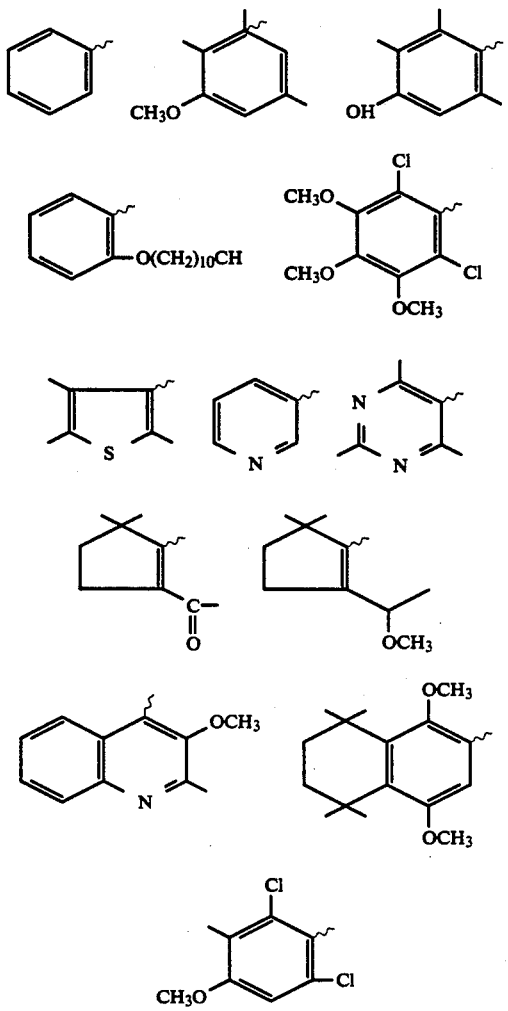

The group R can have the meanings COOH, CONHC$_2$H$_5$, COOC$_2$H$_5$.

Especially preferred compounds in this family are motretinide and etretinate. Other retinoids which are usable according to the invention correspond to the following formulae or their physiologically acceptable salts or esters.

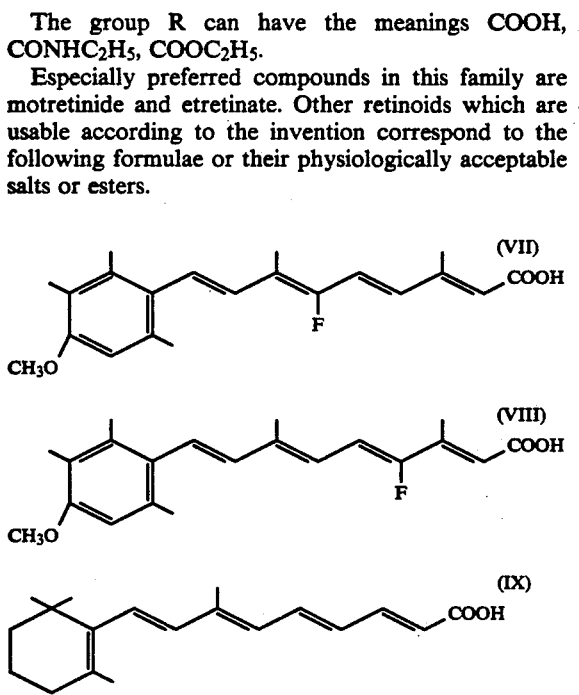

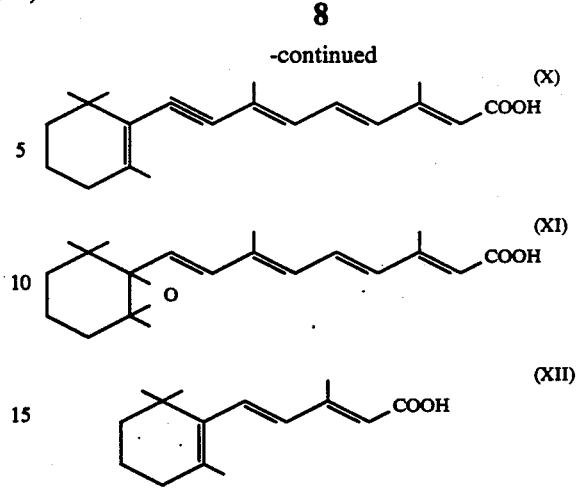

The compounds of the retinoid family which are usable according to the invention are, in particular, described in U.S. Pat. Nos. 4,190,594 and 4,126,698, EP-A-010,209, EP-A-010,208, EP-A-09,776, French Patent 2,293,193 and EP-A-033,095, or in Cancer Research 40,3413-3425, October 1980 or in Annals of the New York Academy of Sciences, Vol. 359.

Especially preferred retinoids are those corresponding to the general formula (II) shown above in which R$_1$ denotes a radical

in which X denotes OH or OY, Y denoting an alkyl group having from 1 to 15 carbon atoms, it also being possible for X to denote an amino group optionally mono- or disubstituted with a lower alkyl group preferably having 1 to 6 carbon atoms, it also being possible for R to denote a —CH$_2$OH or —CHO group, and A denoting a group:

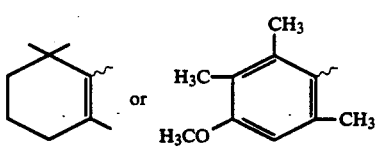

these compounds preferably being in the form of the all-trans or 13-cis isomers.

Among especially preferred derivatives, there may be mentioned the products commonly designated tretinoin, isotretinoin, retinol, motretinide and etretinate, retinol derivatives such as the acetate, palmitate or propionate and zinc all-trans-retinoate, and still more especially tretinoin or all-trans retinoic acid.

The retinoids used according to the invention can be present in the same composition as the pyrimidine derivative and sunscreen agent, and preferably in proportions of between 0.001 and 2% by weight, and especially between 0.01 and 0.5% by weight, relative to the total weight of the composition.

Another form of the invention can consist of a combination comprising a component (A) consisting of the composition based on the pyrimidine derivative of the formula (I) and the sunscreen agent defined above, and a component (B) containing a retinoid in a physiologically acceptable medium.

The physiologically acceptable medium can be of the type defined above in relation to the composition containing the pyrimidine derivative of the formula (I) and the sunscreen agent.

The retinoid is present in the component (B) in the proportions stated above, namely preferably between 0.001 and 2% by weight, and especially between 0.01 and 0.5% by weight, relative to the total weight of the component (B).

The treatment of the scalp for the purpose of inducing and stimulating hair growth and decreasing its loss may be performed according to a process consisting, according to a first variant, in applying, in a first stage, the combination according to the invention consisting of a component (A) containing the pyrimidine derivative of the formula (I) and the agents screening out UV radiation, defined above, in a physiologically acceptable medium.

According to a second variant, a component (B) consisting of a composition containing a retinoid as defined above in a physiologically acceptable medium is applied either simultaneously, or successively, or even after an interval of time.

According to an especially preferred embodiment of the invention, the component (B) containing the retinoid is applied first and, after a contact time of one minute to 12 hours, the component (A) containing the pyrimidine derivative of formula (I) with the agent screening out UV radiation is applied.

It is also possible, according to a third especially preferred variant, to mix the components (A) and (B) at the required time immediately before use.

The application is preferably performed using doses of 0.5 to 2 cm³ of each of the components or of the two components combined in a mixture prepared at the time of use.

The combination according to the invention, and more especially in the variant employing the component (A) and the component (B), may be packaged in the form of a multi-compartment device also known as a "kit" or outfit, the first compartment of which contains the component (A) based on the pyrimidine derivative of the formula (I) and the agent screening out UV radiation as defined above, and a component (B) containing a retinoid in a physiologically acceptable medium.

Another subject of the invention consists of a process for solubilizing a pyrimidine derivative of formula (I), as a result of the concomitant use of an agent screening out UV radiation as defined above.

The process according to the invention relates essentially to a therapeutic treatment for hair loss by acting especially on the functions and the biological mechanism at the origin of hair growth, and in particular via an action on this growth mechanism by prolonging the anagen phase.

This process according to the invention may also be applied in the context of a cosmetic treatment, inasmuch as it enables the hair to be rendered more attractive by endowing it with greater vigour and an improved appearance.

The examples which follow are intended as an illustration of the invention without, however, being limiting in nature.

EXAMPLE 1

The following composition is prepared:

| | |
|---|---|
| Minoxidil | 3.40 g |
| 2-Hydroxy-4-methoxybenzophenone (UVINUL M 40, sold by the company GAF) | 3.00 g |
| Propylene glycol 6.5 g/ethyl alcohol 93.5 g | qs 100.00 g |

The solubility of minoxidil is increased relative to its solubility in the same medium without the sunscreen.

EXAMPLE 2

The following composition is prepared:

| | |
|---|---|
| Minoxidil | 3.30 g |
| 2-Ethylhexyl p-dimethylaminobenzoate (ESCALOL 507, sold by the company VAN DYK) | 3.00 g |
| Propylene glycol 6.5 g/ethyl alcohol 93.5 g | qs 100.00 g |

The solubility of minoxidil is increased relative to its solubility in the same medium without the sunscreen.

EXAMPLE 3

The following composition is prepared:

| | |
|---|---|
| Minoxidil | 3.20 g |
| 2-Ethylhexyl p-methoxycinnamate (PARSOL MCX, sold by the company GIVAUDAN) | 3.00 g |
| Propylene glycol 6.5 g/ethyl alcohol 93.5 g | qs 100.00 g |

The solubility of minoxidil is increased relative to its solubility in the same medium without a sunscreen.

EXAMPLE 4

The following composition is prepared:

| | |
|---|---|
| Minoxidil | 3.25 g |
| 4-(1,1-Dimethylethyl)-4'-methoxydibenzoylmethane (PARSOL 1789, sold by the company GIVAUDAN) | 3.00 g |
| Propylene glycol 6.5 g/ethyl alcohol 93.5 g | qs 100.00 g |

The solubility of minoxidil is increased relative to its solubility in the same medium without a sunscreen.

EXAMPLE 5

The following components (A) and (B) are prepared and packaged as a kit:

| | |
|---|---|
| Component (A) | |
| Composition of Example 1 | 100.00 g |
| Component (B) | |
| all-trans-Retinoic acid | 0.078 g |
| Butylated hydroxytoluene | 0.025 g |
| Propylene glycol 6.5 g/ethyl alcohol 93.5 g | qs 100.00 g |

A mixture (A+B) in the ratio 60:40 by weight is prepared at the time of use and applied to the scalp on the basis of 1 cm³ per application.

EXAMPLE 6

The following components (A) and (B) are prepared and packaged as a kit:

| | |
|---|---|
| Component (A) | |
| Composition of Example 2 | 100.00 g |
| Component (B) | |
| all-trans-Retinoic acid | 0.062 g |
| Butylated hydroxyanisole | 0.020 g |
| Propylene glycol 6.5 g/ethyl alcohol 93.5 g | qs 100.00 g |

1 cm$^3$ of a mixture (A+B) in equal parts by weight, prepared at the time of use, is applied to the scalp at each application.

EXAMPLE 7

The following composition is prepared:

| | |
|---|---|
| Minoxidil | 6.60 g |
| 2-Ethylhexyl p-methoxycinnamate (PARSOL MCX, sold by the company GIVAUDAN) | 3.00 g |
| Ethyl alcohol 75 g/water 25 g | qs 100.00 g |

The solubility of minoxidil is increased relative to its solubility in the same medium without a sunscreen.

EXAMPLE 8

The following composition is prepared:

| | |
|---|---|
| Minoxidil | 6.10 g |
| N-(2-Ethylhexyl)-3-[(3'-methoxy-4'-n-butoxy)benzylidene]-10-camphor-sulphonamide | 1.00 g |
| Ethyl alcohol 75 g/water 25 g | qs 100.00 g |

The solubility of minoxidil is increased relative to its solubility in the same medium without a sunscreen.

EXAMPLE 9

The following composition is prepared:

| | |
|---|---|
| Minoxidil | 6.20 g |
| Homomenthyl salicylate | 2.00 g |
| Ethyl alcohol 75 g/water 25 g | qs 100.00 g |

The solubility of minoxidil is increased relative to its solubility in the same medium without a sunscreen.

EXAMPLE 10

The following composition is prepared:

| | |
|---|---|
| Minoxidil | 6.10 g |
| 2-Ethylhexyl salicylate | 2.00 g |
| Ethyl alcohol 75 g/water 25 g | qs 100.00 g |

The solubility of minoxidil is increased relative to its solubility in the same medium without a sunscreen.

EXAMPLE 11

The following composition is prepared:

| | |
|---|---|
| Minoxidil | 4.10 g |
| 2-Hydroxy-4-methoxybenzophenone-5-sulphonic acid | 2.00 g |
| Ethyl alcohol 40.5 g/water 59.5 g | qs 100.00 g |

The solubility of minoxidil is increased relative to its solubility in the same medium without a sunscreen.

The compositions of Example 8 to 11 are applied to the alopecic areas of the scalp having a surface area of 100 to 200 cm$^3$ on the basis of 2 ml per day for 3 months.

EXAMPLE 12

The following composition is prepared:

| | |
|---|---|
| Minoxidil | 3.10 g |
| p-Aminobenzoic acid | 2.30 g |
| Ethyl alcohol 40.5 g/water 59.5 g | qs 100.00 g |

The solubility of minoxidil is increased relative to its solubility in the same medium without a sunscreen.

EXAMPLE 13

The following composition is prepared:

| | |
|---|---|
| Minoxidil | 6.30 g |
| Pentyl p-dimethylamino benzoate | 3.00 g |
| Ethyl alcohol 75 g/water 25 g | qs 100.00 g |

The solubility of minoxidil is increased relative to its solubility in the same medium without a sunscreen.

EXAMPLE 14

The following composition is prepared:

| | |
|---|---|
| Minoxidil | 5.80 g |
| 3-(4-Methylbenzylidene)camphor | 3.00 g |
| Ethyl alcohol 75 g/water 25 g | qs 100.00 g |

The solubility of minoxidil is increased relative to its solubility in the same medium without a sunscreen.

EXAMPLE 15

The components (A) and (B) are prepared and packaged as a kit:

| | |
|---|---|
| Component (A) | |
| Minoxidil | 4.70 g |
| N-(2-Ethylhexyl)-3-[(3'-methoxy-4'-n-butoxy)benzylidene]-10-camphorsulphonamide | 0.30 g |
| Ethyl alcohol 75 g/water 25 g | qs 100.00 g |
| Component (B) | |
| all-trans-Retinoic acid | 0.031 g |
| Butylated hydroxyanisole | 0.010 g |
| Propylene glycol 6.5 g/ethyl alcohol 93.5 g | qs 100.00 g |

The two compositions (A) and (B) are applied to an alopecic area of the scalp, separately or separated by an interval of time, either one after the other, (A) in the morning and (B) in the evening, or vice versa, or at an interval of time from 5 minutes to a few hours.

EXAMPLE 16

The components (A) and (B) are prepared and packaged as a kit:

| Component (A) | |
|---|---|
| Minoxidil | 4.70 g |
| Homomenthyl salicylate | 0.50 g |
| Ethyl alcohol 75 g/water 25 g | qs 100.00 g |
| Component (B) | |
| all-trans-Retinoic acid | 0.031 g |
| Butylated hydroxyanisole | 0.010 g |
| Propylene glycol 6.5 g/ethyl alcohol 93.5 g | qs 100.00 g |

The two compositions (A) and (B) are applied to an alopecic area of the scalp, separately or separated by an interval of time, either one after the other, (A) in the morning and (B) in the evening, or vice versa, or at an interval of time from 5 minutes to a few hours.

EXAMPLE 17

The following two compositions (A) and (B) are packaged as a kit:

| Component (A) | |
|---|---|
| Minoxidil | 3.00 g |
| 2-Hydroxy-4-methoxybenzophenone-5-sulphonic acid | 1.00 g |
| Ethyl alcohol 40.5 g/water 59.5 g | qs 100.00 g |
| Component (B) | |
| all-trans-Retinoic acid | 0.031 g |
| Butylated hydroxytoluene | 0.0125 g |
| Propylene glycol 6.5 g/ethyl alcohol 93.5 g | qs 100.00 g |

The two compositions (A) and (B) are applied to an alopecic area of the scalp, separately or separated by an interval of time, either one after the other, (A) in the morning and (B) in the evening, or vice versa, or at an interval of time from 5 minutes to a few hours.

For the different composition of Examples 1 to 17, virtually no crystallization of minoxidil on the scalp is noted.

We claim:

1. A composition for inducing and stimulating hair growth and for decreasing hair loss, said composition comprising, in a physiologically acceptable aqueous or anhydrous medium:

(a) at least an effective concentration of at least one pyrimidine derivative having the formula:

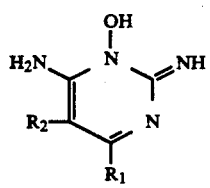

or of an acid addition salt thereof with a physiologically acceptable acid; and (b) a sufficient concentration of at least one compound or mixture of compounds that screens out ultraviolet (UV) radiation to increase the solubility of said pyrimidine derivative in said medium compared to the solubility of the pyrimidine in the same medium in the absence of said compound or mixture of compounds that screens out UV radiation, wherein:

$R_1$ is a group having the formula

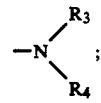

$R_3$ and $R_4$ are either selected from the group consisting of hydrogen, lower alkyl, alkenyl, alkylaryl and cycloalkyl, in which the alkyl portions are lower alkyl, or $R_3$ and $R_4$ with the nitrogen to which they are each bound form a heterocyclic group, which is unsubstituted or is substituted on the carbon atoms with one to three lower alkyl, hydroxy, or alkoxy groups, and which is selected from the group consisting of aziridinyl, azetidinyl, pyrrolidinyl, piperidino, hexahydroazepinyl, heptamethyleniminio, octamethyleneimino, morpholino and 4-(lower alkyl) piperazinyl;

$R_2$ is selected from the group consisting of hydrogen, lower alkyl, alkenyl, alkoxyalkyl, cycloalkyl, aryl, alkylaryl, arylalkyl, alkylarylalkyl, alkoxyarylalkyl and haloarylalkyl, in which the alkyl portions are lower alkyl radicals; and said effective concentration of pyrimidine derivative is effective for inducing and stimulating the growth of hair and reducing its loss;

said UV screening compound is selected from the group consisting of 2-hydroxy-4-methoxybenzophenone, 2-ethylhexyl paradimethylaminobenzoate, pentyl para-dimethylaminobenzoate, 2-ethylhexyl para-methoxycinnamate, 4-(1,1-dimethylethyl)-4'-methoxydibenzolymethane, N-(2-ethylhexyl)-3-[(3'-methoxy-4'-n-butoxy)benzylidene]-10-camphorsulphonamide, 3-(4-methylbenzylidene)camphor, homomenthyl salicylate, 2-ethylhexyl salicylate, para-aminobenzoic acid and 2-hydroxy-4-methoxybenzophenone-5-sulphonic acid;

said aqueous medium consists essentially of water or a mixture of water and a physiologically acceptable solvent; and said anhydrous medium is a physiologically acceptable solvent or mixture of solvents that contains less than 1% water.

2. A process for cosmetically treating the hair, comprising applying an effective amount of at least one combination of claim 10 to the scalp, wherein said amount is effective for cosmetically improving the appearance of the hair.

3. A process for therapeutically treating alopecia, comprising applying an effective amount of the composition of claim 22 to the hair for treating said alopecia.

4. A process for therapeutically treating alopecia, comprising applying an effective amount of the combination of claim 10 to the hair for treating said alopecia.

5. The composition of claim 1, wherein the concentration of the pyrimidine derivative is greater than the solubility limit of said pyrimidine derivative in said medium in the absence of said compound or mixture of compounds that screens out UV radiation.

6. The composition of claim 1, wherein the UV screening compound is 4-(1,1-dimethylethyl)-4'-methoxydibenzoylmethane.

7. The composition of claim 1, wherein $R_2$ is hydrogen and $R_1$ is a

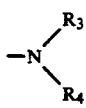

piperidyl ring.

8. The composition of claim 1, wherein the concentration of the pyrimidine derivative of formula (I) is between 0.1 and 10% by weight relative to the total weight of the composition.

9. The composition of claim 1, wherein said sufficient concentration is between 0.1 and 10% by weight relative to the total weight of the composition.

10. The composition of claim 1, wherein said medium is an anhydrous medium.

11. The composition of claim 10 wherein said medium contains a solvent or mixture of solvents selected from the group consisting of $C_2$–$C_4$ lower alcohols, alkylene glycols and alkylene glycol or dialkylene glycol alkyl ethers.

12. The composition of claim 1, wherein said medium is an aqueous or an aqueous-alcoholic medium.

13. The composition of claim 12, wherein said medium contains water and a solvent or mixture of solvents selected from the group consisting of lower alcohols, alkylene glycols and alkylene glycol or dialkylene glycol alkyl ethers.

14. A combination that is effective for inducing and stimulating the growth of hair and reducing its loss, comprising:
(a) a composition of claim 2, and
(b) a second composition containing, in a physiologically acceptable medium, an effective concentration of at least one retinoid, wherein said effective concentrations of pyrimidine derivative and retinoid are effective, when used in said combination, for inducing and stimulating the growth of hair and reducing its loss.

15. Combination according to claim 14, wherein the retinoid is selected from the compounds of formula:

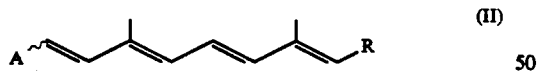

in which:
(a) A is a group selected from the groups of formulae:

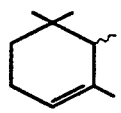

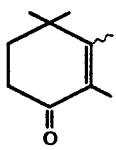

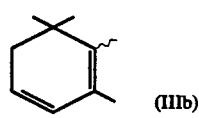

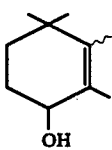

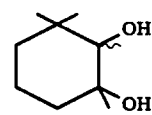

when A denotes a group of formula (IIIa), R is selected from the following groups:
CHO; $CH_2OR_5$,
in which $R_5$ denotes hydrogen or $C_1$–$C_4$ lower alkyl;
a group

where $R_6$ denotes $C_1$–$C_{16}$ linear or branched alkyl;
$CH_2SR_7$, in which $R_7$ denotes hydrogen or methyl;

in which X denotes:
(i) OH;
(ii) $OR_8$, where $R_8$ denotes a $C_1$–$C_{15}$ alkyl radical, $C_1$–$C_4$ arylalkyl radical optionally substituted on the aryl group, $C_1$–$C_4$ arylcarboxyalkyl radical optionally substituted on the aryl group, or $C_1$–$C_4$ hydroxyalkyl or $C_1$–$C_4$ amidoalkyl radical;
(iii) $NR_9R_{10}$, in which $R_9$ and $R_{10}$, which may be identical or different, denote hydrogen, $C_1$–$C_6$ alkyl, $C_1$–$C_4$ hydroxyalkyl or optionally substituted aryl;
it being possible for $R_9$ or $R_{10}$ to represent an optionally substituted heterocycle or, together with the nitrogen atom to which they are attached, to form a heterocycle which is itself optionally substituted;
(iv) an $N_3$ group;
or alternatively a group of formula $CH_2NHR_{11}$, in which $R_{11}$ denotes an optionally substituted benzoyl radical;

when A denotes a group of formula (IIIb), (IV), (V) or (VI), $R_1$ denotes COOH as well as its salified or esterified form;

b) A is a group selected from aryl or substituted aryl groups, a heterocycle or substituted heterocycle, an aryl-heterocyclic group optionally substituted on the heterocycle or an aryl-homocyclic group optionally substituted on the aromatic ring, $R_1$ in this case denoting a COOH group, a group $COOR_{12}$ where $R_{12}$ denotes a $C_1$–$C_4$ alkyl radical or alternatively an amide group substituted with a $C_1$–$C_4$ alkyl group, as well as their physiologically acceptable salts and esters.

16. Combination according to claim 14, wherein the retinoid is selected from retinal, retinol, retinyl acetate, propionate and palmitate, retinoic acid in all-trans, 13-cis, 9-cis, 11-cis, 9,13-dicis and 11,13-dicis forms, the corresponding zinc retinoates and the quaternary ammonium retinoates of formula:

$$R_{16}-\overset{\overset{R_{13}}{|}}{\underset{\underset{R_{14}}{|}}{N^{\oplus}}}-R_{15} \quad X^{\ominus} \qquad (VII)$$

in which $X^{\ominus}$ denotes an all-trans- or 13-cis-retinoate radical; and (i) $R_{13}$, $R_{14}$ and $R_{15}$, which may be identical or different, denote a $C_1$–$C_4$ linear alkyl group which can bear one or more hydroxyl group(s) in the chain, $R_{16}$ denoting $C_{12}$–$C_{18}$ linear alkenyl or alkyl;

(ii) $R_{15}$ denotes a group:

$$-(CH_2)_n-\underset{}{\bigcirc}-R_{17}$$

in which:

n is equal to 0 or 1, $R_{17}$ represents a hydrogen or halogen atom or a hydroxyl, $C_1$–$C_{18}$ alkyl or hydroxyalkyl or $C_2$–$C_{18}$ acyl group;

$R_{13}$, $R_{14}$ and $R_{15}$ having the meanings stated under (i);

(iii) $R_{13}$ and $R_{14}$ can form an aliphatic heterocycle containing at least one oxygen atom, one nitrogen atom or one sulphur atom;

$R_{15}$ or $R_{16}$ having the meanings stated under (i) and (ii);

all-trans-retinoyloxyacetamide, a mixture of 2-hydroxy-1-propyl and 1-hydroxy-2-propyl all-trans-retinoates, 2-hydroxyethyl all-trans-retinoate, 4-nitrobenzyl all-trans-retinoate, benzyl all-trans-retinoate, 4-(all-trans-retinoyloxyacetyl)catechol, 2-cyclohexylethyl all-trans-retinoate, 10-carboxymethyldecyl all-trans-retinoate, 4-hydroxybutyl all-trans-retinoate, cholesteryl all-trans-retinoate, 4-bromobenzyl all-trans-retinoate, cholesteryl all-trans-retinoyloxyacetate, all-trans-retinoyloxyacetylbenzene, 4-(all-trans-retinoyloxyacetyl)bromobenzene, 4-(all-trans-retinoyloxyacetyl)nitrobenzene, 4-(all-trans-retinoyloxyacetyl)benzonitrile, all-trans-retinoyloxyacetyl-2,4-dichlorobenzene, N-(all-trans-retinoyloxy)phthalimide, N-(all-trans-retinoyloxy)succinimide, 4-(all-trans-retinoyloxyacetyl)methoxybenzene, 4-(all-trans-retinoyloxyacetyl)phenol, 4-(all-trans-retinoyloxyacetyl)-3,4,5-trimethoxybenzene, 4-(all-trans-retinoyloxyacetyl)-2,4,6-trimethylbenzene, 4-(all-trans-retinoyloxyacetyl)toluene, 4-(all-trans-retinoyloxyacetyl)ethoxybenzene, 4-(all-trans-retinoyloxyacetyl)acetoxybenzene, 4-(all-trans-retinoyloxyacetyl)naphthalene, 4-(all-trans-retinoyloxyacetyl)biphenyl, 4-(all-trans-retinoyloxyacetyl)-2,5-dimethoxybenzene, 1-(all-trans-retinoyloxyacetyl)-2,4-dimethylbenzene, 1-(all-trans-retinoyloxyacetyl)-3,4-diacetoxybenzene, all-trans-retinamide, 2-hydroxyethyl all-trans-retinamide, N-ethyl-all-trans-retinamide, 4-(all-trans-retinoyl)aminophenol, N-(methyldimethyldioxolane)retinamide, N-(ortho-carboxyphenyl)retinamide, N-(p-carboxyphenyl)retinamide, N-hydroxypropylall-trans-retinamide, N-(hydroxypropyl)-13-cis-retinamide, N-(5-tetrazolyl)-all-trans-retinamide, N-(5-tetrazolyl)-13-cis-retinamide, N-(3,41-methylenedioxyphenylmethyl)-all-trans-retinamide, N-(n-propyl)-all-trans-retinamide, N-tert-butyl-all-trans-retinamide, N-(1,1,3,3-tetramethylbutyl)-all-trans-retinamide, N-(4-carboxymethyl-3-hydroxyphenyl)-all-trans-retinamide, N-[β-(3,4-dimethoxyphenyl)ethyl]-all-trans-retinamide, 2-(all-trans-retinoylamino)benzotriazole, 1-(all-trans-retinoyl)-1,2,4-triazole, N-(all-trans-retinoyl)imidazole, 1-nicotinoyl-2-(all-trans-retinoyl)hydrazine, N-(all-trans-retinoyl)morpholine, trans-β-ionone (all-trans-retinoyl)hydrazone, N,N'-dicyclohexyl-N-(all-trans-retinoyl)urea, acetone (all-trans-retinoyl)hydrazone, N-benzoylretinylamine and retinoyl azide.

17. Combination according to claim 14, wherein retinoids correspond to formula (II) in which:

a denotes any one of the following groups:

and R denotes COOH, $CONHC_2H_5$ or $COOC_2H_5$.

18. Combination according to claim 14, wherein the retinoid is selected from the compounds of formulae:

(VII)

-continued

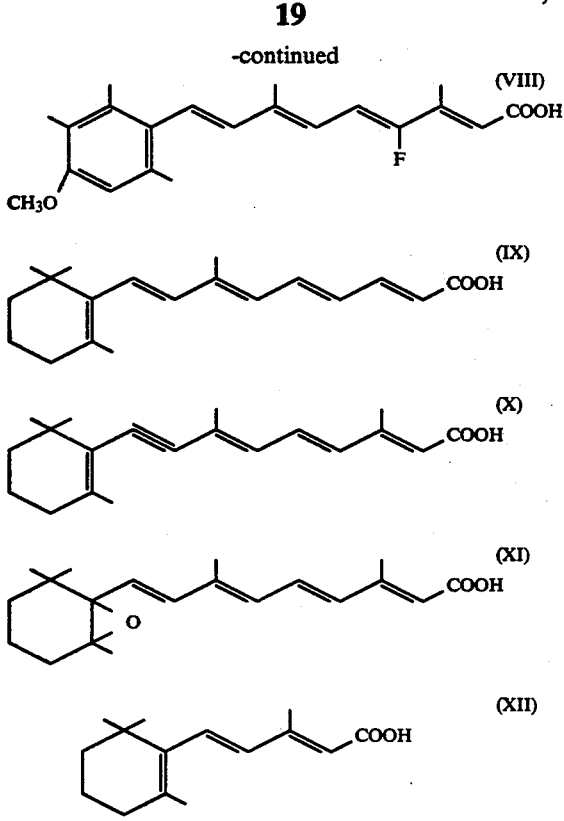

as well as their physiologically acceptable salts or esters.

19. Combination according to claim 14 wherein the retinoid is selected from the compounds of formula (II):

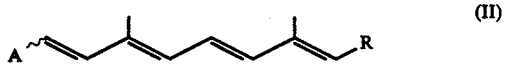

in all-trans or 13-cis form, in which $R_1$ denotes a group

where X can denote an OH group or a group OY, Y denoting an alkyl group having 1 to 15 carbon atoms, it also being possible for X to denote an amino group, optionally mono- or disubstituted with a lower alkyl group having 1 to 6 carbon atoms, $R_1$ also denoting a —CH$_2$OH or —CHO group, and A denoting a group:

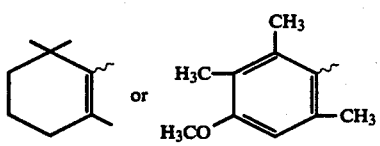

as well as the pharmaceutically or cosmetically acceptable salts.

20. Combination according to claim 14, wherein the retinoid is selected from tretinoin, isotretinoin, retinol or vitamin A and its derivatives such as the acetate, palmitate or propionate, motretinide, etretinate and zinc all-trans-retinoate.

21. Combination according to claim 14, wherein the components (A) and (B) form part of one and the same composition.

22. Combination according to claim 14, wherein the components (A) and (B) are intended for mixing at the required time immediately before use.

23. Combination according to claim 14, wherein the components (A) and (B) are intended for application separately or separated by an interval of time.

24. Combination according to claim 14, wherein the component (B) contains the retinoid in proportions of between 0.001 and 2% by weight relative to the total weight of the composition.

25. Multi-compartment device, comprising at least two compartments, one of which contains the component (A) and the other the component (B) as defined in claim 14.

26. A composition of claim 1, wherein said effective concentration of pyrimidine derivative is sufficient for use of said composition in the therapeutic treatment of alopecia.

27. A combination of claim 14, wherein said effective concentrations of pyrimidine derivative and retinoid are sufficient, when used in said combination, for use of said combination in the therapeutic treatment of alopecia.

28. A process for cosmetically treating the hair, comprising applying an effective amount of at least one composition of claim 1 to the scalp, wherein said amount is effective to cosmetically improve the appearance of the hair.

29. Method of treatment according to claim 28, wherein the component (B) containing the retinoid is applied in a first stage, and wherein, after a contact time of one minute to 12 hours, the component (A) containing the pyrimidine derivative of formule (I) and the agent screening out UV radiation is applied.

30. Process for cosmetic treatment of the scalp, wherein a composition resulting from a mixture of the components (A) and (B) of the combination defined in claim 14 is applied to the scalp.

31. Process for solubilizing a pyrimidine derivative corresponding to the formula (I), defined in claim 1, in a physiologically acceptable medium, wherein at least one sunscreen selected from 2-hydroxy-4-methoxybenzophenone, 2-ethylhexyl para-dimethylamino-benzoate, pentyl para-dimethylaminobenzoate, 2-ethylhexyl para-methoxycinnamate, 4-(1,1dimethylethyl)-4'-methoxy dibenzoylmethane, N-(2-ethylhexyl)-3-[(3'-methoxy-4'-n-butoxy)benzylidene]-10-camphorsulphonamide, 3-(4-methyl-benzylidene)camphor, homomenthyl and 2-ethylhexyl salicylates, para-aminobenzoic acid and 2-hydroxy-4-methoxy-benzophenone-5-sulphonic acid and 2-hydroxy-4-methoxy-benzophenone-5-sulphonic acid is added to the physiologically acceptable medium.

* * * * *